United States Patent [19]

Virtanen

[11] Patent Number: 4,668,218
[45] Date of Patent: May 26, 1987

[54] INDICATING MEANS FOR A DOSAGE DISPENSING DEVICE

[75] Inventor: Risto Virtanen, Nurmijärvi, Finland

[73] Assignee: Aktiebolaget Draco, Sweden

[21] Appl. No.: 850,959

[22] Filed: Apr. 11, 1986

[30] Foreign Application Priority Data

Apr. 12, 1985 [SE]  Sweden ............................... 8501806

[51] Int. Cl.⁴ ............................................. A61M 13/00
[52] U.S. Cl. ................................ 604/58; 128/203.15;
221/7; 116/299
[58] Field of Search .................................... 604/57–59;
128/203.15; 116/299, 305, 309, 317; 221/2, 4, 5, 7, 8, 82, 83, 87

[56] References Cited

U.S. PATENT DOCUMENTS

| | | | |
|---|---|---|---|
| 508,935 | 11/1893 | Gerry .................................. | 116/299 |
| 786,073 | 3/1905 | Walsh . | |
| 1,668,617 | 5/1928 | Vermillian .......................... | 116/299 |
| 3,688,945 | 9/1972 | Harman, Jr. et al. ................. | 221/8 |
| 4,034,757 | 7/1977 | Glover . | |
| 4,147,166 | 4/1979 | Hansen ............................ | 128/203.15 |

FOREIGN PATENT DOCUMENTS 146343 5/1981 Norway .
2129691 5/1984 United Kingdom ........... 128/203.15

Primary Examiner—C. Fred Rosenbaum
Assistant Examiner—Jerome R. Smith, Jr.
Attorney, Agent, or Firm—Brumbaugh, Graves, Donohue & Raymond

[57] ABSTRACT

An indicating means in a dosage dispensing device for medicaments, particularly a dosage inhaler which indicates a number of dosages administered from the dosage dispensing device. The indicating means includes a rotatable disc (1) having apertures (2) passing therethrough which can be filled with a medicament in particle form. By rotating the disc the apertures can be brought into an air channel or duct (3) through which air is inhaled. The rotatable disc has associated with a central portion a spiral groove or ridge (4) which can engage with peripheral teeth (8) on a toothed wheel (6), such that rotation of the disc (1) results in rotation of the toothed wheel and the toothed wheel is provided with one or more markings (9) which are visible from outside the dosage inhaler upon rotating the disc a predetermined number of times.

10 Claims, 5 Drawing Figures

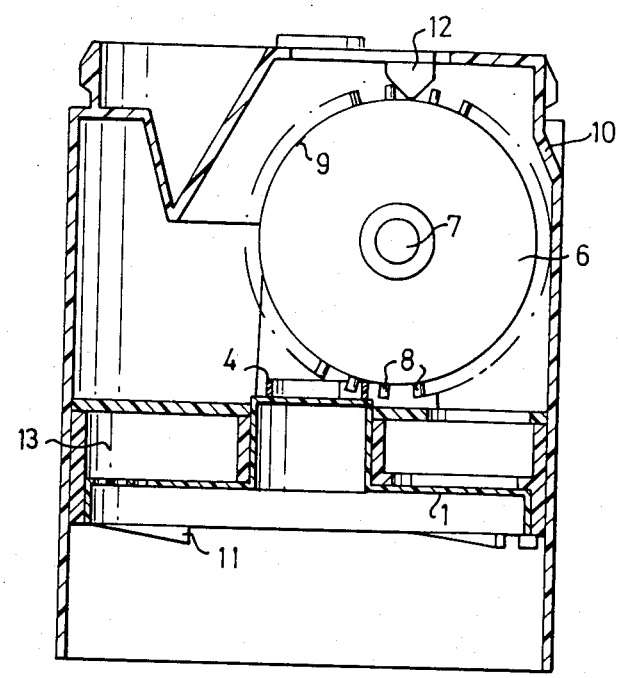
FIG.1
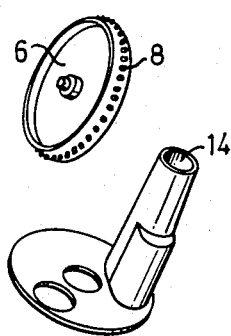
FIG.2
FIG.3
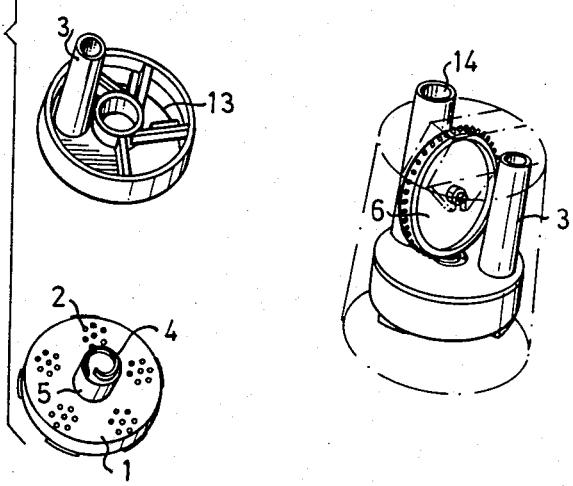

INDICATING MEANS FOR A DOSAGE DISPENSING DEVICE

TECHNICAL FIELD

The present invention relates to an indicating means for a dosage dispensing device for medicaments, and in particular to an indicating means for a dosage inhaler, effective to indicate a number of medicament dosages administered. A dosage dispensing device, and in particular a dosage inhaler, provided with indicating means constitutes a further aspect of the invention.

One object of the invention is to provide an indicating means which will clearly indicate to the user a given number of dosages administered, and primarily a number at which the store of medicament in the dosage dispensing device is exhausted. A further object is to provide an indicating means which can be used to indicate small quantities of medicament which are difficult to discern by direct observation.

BACKGROUND PRIOR ART

Inhalers intended for medicaments in powder form are known to the art. EP No. 0069715 describes and illustrates one such device in which the powder is metered in given dosages through apertures located in a rotatable disc, these apertures being introduced into an airduct or channel through which air is inhaled, by rotating the disc. A characteristic feature of this type of inhaler is that it is used to administer a precise amount, or dosage, of highly potent medicaments, which are consequently metered in extremely small amounts, for example 0.1 mg. The stored amount of medicament is also kept small, for example 10-30 mg. Such a small quantity, and the change therein, cannot readily be discerned by direct observation. In this case there is a risk of the supply of medicament becoming exhausted without the patient noticing the fact in time, which results in the patient missing his/her treatment with the subsequent risk to the wellbeing of the patient. Consequently, there is a need for an indicator which will readily indicate a number of dosages administered in a clear and unambiguous fashion.

The need for indicating the number of dosages measured in the aforesaid minute quantities of medicinal substances is also found in dosage dispensing devices other than dosage inhalers.

BRIEF DESCRIPTION OF THE INVENTION

The present invention starts from the concept of an indicating means for a dosage dispensing device for medicaments, particularly for a dosage inhaler, in which the means comprise a rotatable disc provided with apertures passing therethrough which can be filled with a medicament in particle form and which, by rotating the disc, can be placed in register with an airduct or channel through which air is inhaled.

The invention of the present Application resides in the fact that the rotatable disc has associated with the central portion thereof a spiral groove or ridge which is engageable by teeth located on the periphery of a toothed wheel and extending transverse to the spiral groove or ridge, such that rotation of the disc results in rotation of the toothed wheel and in that the toothed wheel is provided with one or more markings which are visible from outside the dosage inhaler upon rotation of the disc a predetermined number of times.

The toothed wheel may be positioned at any angle to the disc, with the teeth extending transverse to the spiral groove or ridge on the rotatable disc, however. The toothed wheel preferably extends in a diametral plane of disc with the spiral groove or ridge arranged to draw the teeth of the toothed wheel in towards the center of the disc when the disc is rotated in its intended direction of rotation. To this end, the spiral groove or ridge is preferably so arranged that its outermost part is located at a shorter radial distance from the center of the disc than the projection of the axis of the shaft of the toothed wheel on the disc. Advantageously a latching means is arranged for resilient engagement between the teeth of the toothed wheel to prevent the wheel from rotating other than when caused to rotate by rotation of the disc.

The marking or markings which can indicate a number of dosages corresponding, for example, to a substantially all or half of the quantity of medicaments stored in a device, or to a number of dosages prescribed for a given period of time are, in accordance with the preferred embodiment of the invention, arranged so that each marking is visible in a window provided in the outer wall of the dosage inhaler.

The invention also provides a dosage inhaler incorporating the indicating means of the invention, together with a medicament storage space and an air duct through which air is inhaled, the apertures in the rotatable disc being capable of being brought into register with the air duct.

The invention will now be described in more detail with reference to an embodiment thereof illustrated in the accompanying drawings, in which FIG. 1 is a side elevation in section of the upper part of one embodiment of dosage inhaler incorporating indicating means according to the present invention;

FIG. 2 is a perspective of the internal components of the dosage inhaler shown in FIG. 1;

FIG. 3 is an exploded perspective view of the components shown in FIG. 2;

Figure 4:
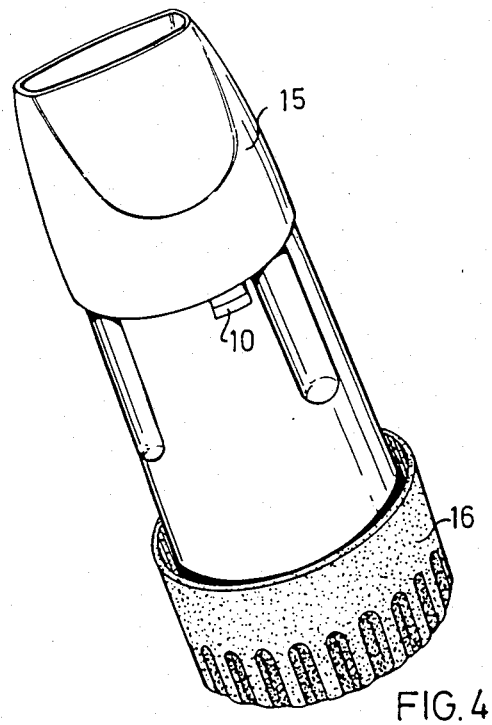
FIG. 4 illustrates in perspective the external configuration of a dosage inhaler according to the invention provided with a mouthpiece.
Figure 5:
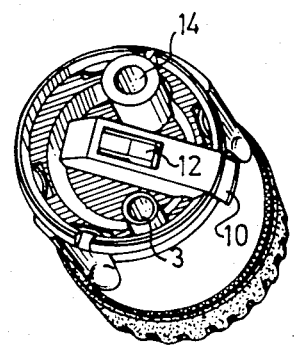
FIG. 5 illustrates in perspective the external configuration of the dosage inhaler according to the invention in the absence of a mouthpiece.

In the drawings, a rotatable disc 1 forms part of a dosage inhaler and has located on the surface thereof a number of groups of apertures 2 which pass through the disc. In one rotational position of the disc, a group of apertures can be filled with medicament in particle form and then be rotated to a position in which they lie in register with an airduct 3 through which the medicament can be inhaled. An indicating means is provided by a spiral groove or ridge 4 mounted on the end of a central shaft 5 connected to the disc 1, and a toothed wheel 6 is mounted above and in a diametral plane of the disc 1, and rotatable about an axis perpendicular to the axis of the disc, on a shaft 7 journalled in the dosage inhaler. The toothed wheel 6 has arranged around its periphery a plurality of radially projecting teeth 8, of which at least one engages the spiral groove or ridge 4 in a manner such that rotation of the disc 1 results in rotation of the toothed wheel 6. Located on the periphery of the toothed wheel is a colour marking 9, which can be brought into view in a window 10 provided in the outer wall of the dosage inhaler, by rotating the toothed wheel.

The disc 1 is provided with ratchet teeth 11, by means of which the disc can be rotated in the desired direction. The spiral groove or ridge 4 is so arranged that upon rotation of the disc in this desired direction that tooth, or those teeth, of the toothed wheel 6 engaging the spiral groove or ridge 4 is, or are, drawn towards the center of the disc 1. The toothed wheel is so positioned that the projection of the axis of the shaft 7 on the disc lies at a greater radial distance from the center of the disc than the outer most part of the spiral groove or ridge 4. Arranged above the toothed wheel 6 is a latching means 12 in the form of a latching pawl arranged to engage between the teeth of the toothed wheel.

In addition to the aforedescribed indicating means according to the invention, the inhaler also incorporates known components necssary for its function, such as a medicament storage compartment 13 and an associated filling channel 14. A mouthpiece 15 encloses the upper part of the inhaler and has a form which enables it to be placed in the mouth of a patient. The rotatable disc 6 is indexed by operating means 16 known per se having a pawl or the like engageable with ratchet teeth 11.

I claim:

1. An indicating means for a dosage dispensing device for medicaments, particularly a dosage inhaler, said means comprising a rotatable disc; apertures passing through said disc, said apertures being fillable with a medicament in particle form; an airduct or channel through which air can be inhaled; means for rotating said disc effective to bring at least one of said apertures into register with said airduct or channel; a spiral groove or ridge associated with a central portion of said disc; a toothed wheel; peripheral teeth on said wheel extending transverse to and engaging with said spiral groove or ridge, whereby rotation of said disc results in rotation of said toothed wheel; and one or more markings on said toothed wheel which are visible from outside the dosage inhaler upon rotation of the disc a predetermined number of times.

2. An indicating means as claimed in claim 1, wherein said toothed wheel extends in a diametral plane of the disc and the spiral groove or ridge is arranged to draw the teeth of the toothed wheel in towards the center of the disc when the disc is rotated in its intended direction of rotation.

3. An indicating means as claimed in claim 2, wherein the outermost part of the spiral groove or ridge is located at a shorter radial distance from the center of the disc than the projection of the axis of the shaft of the toothed wheel on the disc.

4. An indicating means as claimed in claim 1, and further comprising latching means arranged for resilient engagement between the teeth of the toothed wheel.

5. An indicating means as claimed in claim 1, further comprising a window positioned whereby each marking is arranged to be brought into view in said window on rotation of said disc.

6. A dosage inhaler comprising a medicament storage space; a rotatable disc rotatable adjacent said storage space; apertures passing through said disc, said apertures being fillable with a medicament in particle form from said storage space; an airduct or channel through which air can be inhaled; means for rotating said disc effective to bring at least one of said apertures into register with said airduct or channel; a spiral groove or ridge associated with a central portion of said disc; a toothed wheel; peripheral teeth opposite wheel extending transverse to and engaging said spiral groove or ridge, whereby rotation of said disc results in rotation of said tooth wheel; and one or more markings on said tooth wheel which are visible from outside the dosage inhaler upon rotation of the disc a predetermined number of times.

7. A dosage inhaler as claimed in claim 6, wherein said toothed wheel extends in a diametral plane of the disc and the spiral groove or ridge is arranged to draw the teeth of the toothed wheel in towards the center of the disc when the disc is rotated in its intended direction of rotation.

8. A dosage inhaler as claimed in claim 6, wherein the outer most part of the spiral groove or ridge is located at a shorter radial distance from the center of the disc than the projection of the axis of the shaft of the toothed wheel on the disc.

9. A dosage inhaler as claimed in claim 6, and further comprising a latching means arranged for resilient engagement between the teeth of the toothed wheel.

10. A dosage inhaler as claimed in claim 6, and further comprising a window positioned whereby each marking is arranged to be brought into view of said window on rotation of said disc.

* * * * *